United States Patent [19]

Metz et al.

[11] Patent Number: 5,767,330
[45] Date of Patent: Jun. 16, 1998

[54] PROCESS FOR PREPARING ALKYL CHLORIDES

[75] Inventors: Josef Metz, Marl; Clemens Osterholt, Dorsten; Juergen Lange, Haltern, all of Germany

[73] Assignee: Huels Aktiengesellschaft, Marl, Germany

[21] Appl. No.: 799,035

[22] Filed: Feb. 10, 1997

[30] Foreign Application Priority Data

Feb. 8, 1996 [DE] Germany .................. 196 04 567.3

[51] Int. Cl.$^6$ ........................................ C07C 17/16
[52] U.S. Cl. ..................................................... 570/258
[58] Field of Search .............................. 570/258

[56] References Cited

U.S. PATENT DOCUMENTS 3,981,938  9/1976  Steele et al. .

FOREIGN PATENT DOCUMENTS 645357   3/1995   European Pat. Off. .
934 701 C  11/1955  Germany .

Primary Examiner—Gary Geist
Assistant Examiner—S. Padmanabhan
Attorney, Agent, or Firm—Oblon, Spivak, McClelland, Maier & Neustadt, P.C.

[57] ABSTRACT

The preparation of long-chain alkyl chlorides from alcohols and hydrogen chloride is improved by carrying out the reaction at a temperature below the boiling point of the alkyl chloride, and distilling off the resulting alkyl chloride by feeding in additional hydrochloric acid.

20 Claims, 1 Drawing Sheet

PROCESS FOR PREPARING ALKYL CHLORIDES

BACKGROUND OF THE INVENTION

1. Field of the Invention

The invention relates to a novel process for preparing alkyl chlorides having 6 to 16 carbon atoms, by reacting the corresponding alcohols with hydrogen chloride.

2. Discussion of the Background

Alkyl chlorides are valuable solvents. They are used for Friedel-Crafts syntheses and for preparing organometallic compounds, crop protection agents or pharmaceutical products.

In the preparation of alkyl chlorides, one generally starts from olefins or alcohols. In DE-A-39 17 190, chloroalkanes having 8–22 carbon atoms are prepared in a batch process at 120°–180° C. Myristyl alcohol is converted into tetradecyl chloride, for example, at 135°–145° C. using HCl gas. During the reaction, the reaction water is distilled off as concentrated hydrochloric acid. After the reaction, the reactor contents are worked up by distillation. An approximately 95% pure product is obtained. In this process, ethers are formed in relatively large amounts in a side reaction, which must then be added to following batches.

In JP 74/034 646, for example, n-octyl alcohol is reacted with HCl gas at 130° C., with pyridine as a catalyst, to form n-octyl chloride. The product is distilled off at reduced pressure. The yield here is only 93.6%, based on the alcohol used.

According to JP 73/030 606, n-octanol is reacted with 28.5% strength HCl at 110°–130° C., with quinoline as a catalyst, in a first stage. N-octyl chloride is then distilled off under reduced pressure, and the unreacted n-octanol is reacted with HCl gas in a second stage. In this process, by-product formation is very high.

DE-A-24 35 029 describes the preparation of monochloroalkanes and monochlorocycloalkanes having more than 4 carbon atoms in a reactor having a large surface area. In this process, an HCl-saturated aqueous mixture of $ZnCl_2$ and alcohol is passed from top to bottom, gaseous HCl being allowed to flow in the opposite direction. This process requires a special apparatus and catalyst work up, as well as recycling.

In CZ 148 797, alkyl halides having 1–8 carbon atoms are prepared from the corresponding alcohols. In this process, butyl chloride, for example, is distilled off batchwise with unreacted alcohol and water as an azeotrope. After phase separation, in which the aqueous phase is discarded, the organic phase is recycled. After a plurality of cycles, and only after approximately 12 hours, butyl chloride is obtained at satisfactory conversion rates.

SUMMARY OF THE INVENTION

An object of the present invention is to provide a simple process by which alkyl chlorides can be prepared from alcohols in high space/time yields.

This object is achieved by a process comprising reacting the alcohol and the hydrochloric acid at a temperature below the boiling temperature of the alkyl chloride, and distilling off the resulting alkyl chloride by feeding in additional concentrated hydrochloric acid.

DETAILED DESCRIPTION OF THE INVENTION

Figure 1:
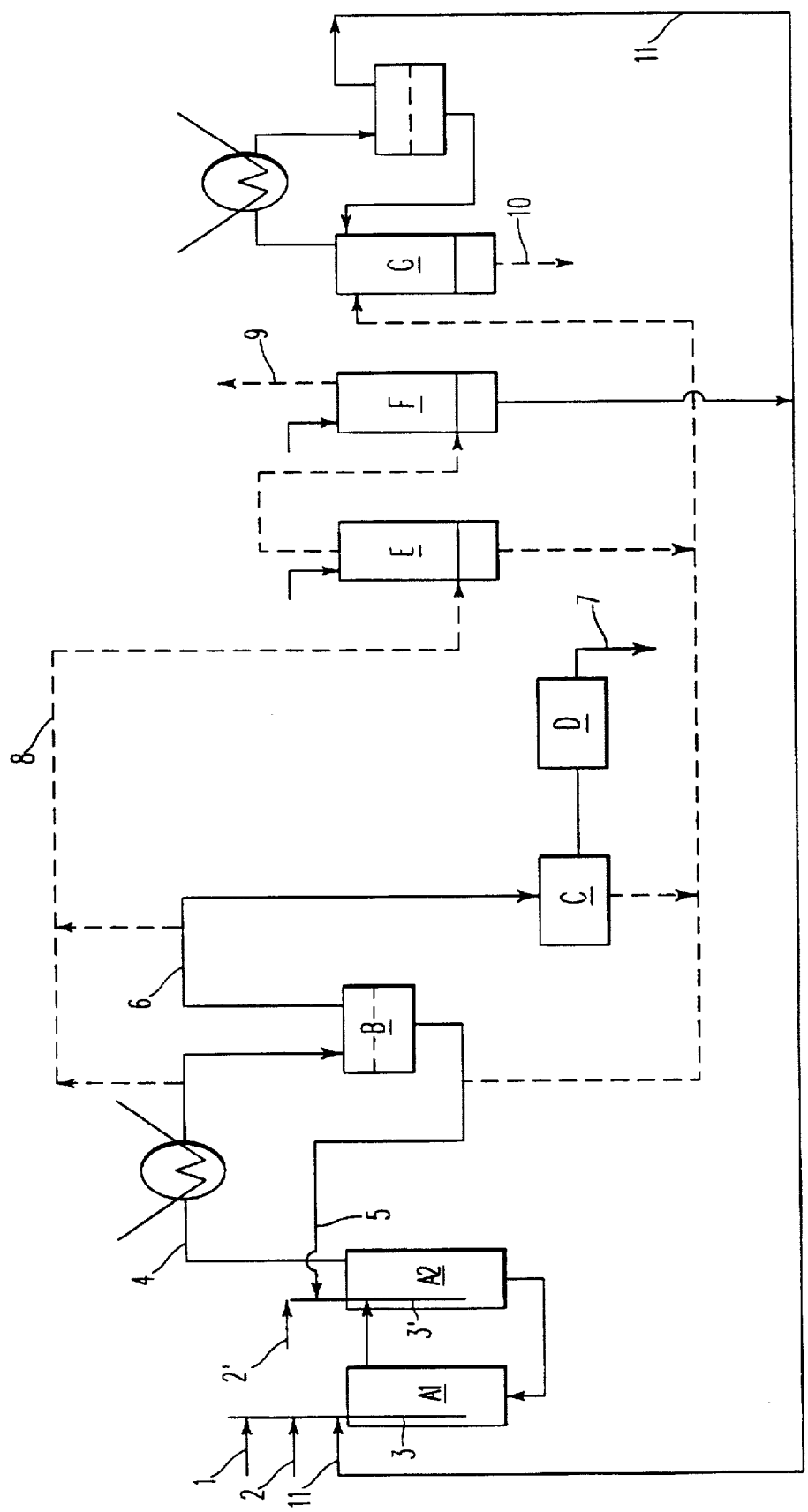
FIG. 1 shows an apparatus and steps described in the Examples.

Alkyl chlorides prepared by the process of the present invention can be linear or branched. Examples include n-hexyl chloride, n-octyl chloride, decyl chloride, dodecyl chloride and tetradecyl chloride. In addition to monochlorides, dichlorides can also be prepared. Preferably, alkyl chlorides having 6–10 carbon atoms are synthesized. Preferably, the reaction temperature is 5°–100° C. below the boiling point of the resulting alkyl chloride.

By introducing a preferably heated concentrated aqueous hydrochloric acid, the product is separated off by a type of steam distillation. Concentrated hydrochloric acids in the context of this invention are 20–45% strength hydrochloric acids, preferably 30–40% strength hydrochloric acids. All strengths of acids are weight percentages, in water.

The process can be carried out batchwise, semicontinuously or continuously. Preferably, the preparation process is performed continuously.

The process gives alkyl chlorides at high space/time yield with improved selectivity. Subsequent work up by distillation is not necessary. The production of residues is small.

Having generally described this invention, a further understanding can be obtained by reference to certain specific examples which are provided herein for purposes of illustration only and are not intended to be limiting unless otherwise specified.

EXAMPLES

Example 1

Continuous Preparation of n-octyl chloride (FIG. 1)

Two series-connected 2 l glass reactors ($A_1$ and $A_2$) are each charged with approximately 1.5 l of an aqueous alkylpyridine hydrochloride solution and set to a reactor temperature of approximately 135° C. The catalyst solution which is introduced is dehydrated in the course of setting the temperature, in accordance with the reactor temperature which has been set.

A mixture of 0.8 mol of n-octanol (1 and 11) and approximately 1 mol of hydrogen chloride (2) are introduced per hour into the reactor $A_1$, via a submerged tube (3).

The reaction product passes via the overflow into reactor $A_2$. There, in addition to a further approximately 0.3 mol of hydrogen chloride (2'), concentrated hydrochloric acid (approximately 36% strength) is additionally added from the line (5) and the reaction product is removed from the top (4) as an azeotrope.

For the azeotropic distillation, a ratio of alkyl chloride-:hydrochloric acid of approximately 1:0.7 is selected. The condensed two-phase distillate is separated in the receiver B. The lower aqueous hydrochloric acid phase is in part recycled (5), and the remainder is passed to the stripping column (G). The upper alkyl chloride phase is worked up and separated via (6) by alkaline scrubbing (C) and alkaline drying (D).

The exhaust gas, predominantly hydrogen chloride and nitrogen, containing a small amount of low-boiling compounds and n-octyl chloride, is fed via the collecting line (8), for the absorption of HCl, to the $H_2O$ counter-current scrubber (E) and then, for the absorption of n-octyl chloride, to the n-octanol counter-current scrubber (F). The exhaust gas (9) thus cleaned can be disposed of, e.g. by exhaust gas combustion.

The n-octyl chloride-enriched n-octanol from the counter-current scrubber (F) is fed into the reactor ($A_1$).

The process waste waters are adjusted to a pH of <7 and fed to the stripping column (G) to remove organic constituents. The upper organic phase of the azeotrope produced there (predominantly olefins, alkyl chlorides, alcohols and aqueous hydrochloric acid) is recycled to the reactor ($A_1$) and the lower aqueous azeotrope phase is passed to the upper section of the stripping column. The bottom phase (10) freed of organic contents is fed to a waste-water treatment plant.

In this cascade procedure, the alcohol conversion rate in the first reactor is approximately 95%, and the remaining conversion is performed in the second reaction stage. Product composition and yield of the n-octyl chloride prepared, according to gas chromatography (GC) analysis, is shown in the Table 1.

TABLE 1

| Low boilers: | 0.7% |
|---|---|
| n-Octyl chloride: | 99% |
| n-Octanol: | 0.2% |
| Di-n-octyl ether: | 0.1% |
| APHA-color: | ≦10 |
| $H_2O$ Content: | ≦300 ppm |
| Yield: | >95% of theoretical prediction |

Example 2
Continuous Preparation of 1,6-dichlorohexane (FIG. 1)

In this case only one reaction stage is required in order to achieve a >99% diol conversion rate, because of the higher reactivity of the diol, in contrast to Example 1.

1.5 l of an aqueous alkylpyridine hydrochloride solution are introduced into the glass reactor (A), and adjusted to 135° C., and a mixture of 0.6 mol of 1,6-hexanediol, approximately 2 mol of hydrogen chloride and concentrated hydrochloric acid in a ratio of diol:hydrochloric acid 0.6:1 is added via the submerged tube (3).

The reaction product (4) discharged in the vapor phase is condensed and the phases are separated in the distillate receiver B. Further work up is performed in a similar manner to Example 1. The counter-current scrubber (F) is operated with 1,6-hexanediol.

Product composition and yield of the 1,6-dichlorohexane prepared, according to GC analysis, is shown in Table 2.

TABLE 2

| Low boilers: | <1% |
|---|---|
| 1,6-Dichlorohexane: | >98% |
| 1,6-Hexanediol: | 0.1% |
| Ether: | <0.3% |
| APHA-color: | ≦10 |
| $H_2O$ content: | ≦300 ppm |
| Yield: | >95% of theory |

Obviously, additional modifications and variations of the present invention are possible in light of the above teachings. It is therefore to be understood that within the scope of the appended claims, the invention may be practiced otherwise than as specifically described herein.

The priority document of the present application, German patent application 196 04 567.3, filed Feb. 8, 1996, is hereby incorporated by reference.

What is claimed as new and desired to be secured by Letters Patent of the United States is:

1. A process for preparing alkyl chlorides, comprising:
   reacting an alcohol with hydrogen chloride, thereby forming a composition comprising an alkyl chloride; and
   adding concentrated hydrochloric acid to said composition, thereby producing a vapor comprising said alkyl chloride;
   wherein said alkyl chloride has 6–16 carbon atoms, and said reacting is carried out at a temperature below the normal boiling point of said alkyl chloride.

2. The process of claim 1, wherein said alkyl chloride has 6–10 carbon atoms.

3. The process of claim 1, wherein said reacting is carried out at 5°–100° C. below the normal boiling point of said alkyl chloride.

4. The process of claim 1, wherein said process is carried out continuously.

5. The process of claim 1, wherein said alkyl chloride is selected from the group consisting of n-hexyl chloride, n-octyl chloride, decyl chloride, dodecyl chloride and tetradecyl chloride.

6. The process of claim 1, wherein said alkyl chloride is a dichloride.

7. The process of claim 1, wherein said concentrated hydrochloric acid has a strength of 30–40%.

8. The process of claim 1, wherein said reacting takes place in the presence of a catalyst.

9. The process of claim 1, further comprising:
   condensing said vapor into a distillate comprising
      (i) a first phase comprising aqueous hydrochloric acid; and
      (ii) a second phase comprising said alkyl chloride; and
   adding said first phase to said composition.

10. The process of claim 1, wherein said process produces said alkyl halide in a yield of at least 95%, based on said alcohol.

11. A process for preparing alkyl chlorides, comprising:
   reacting an alcohol and hydrogen chloride in a first reactor, thereby forming a composition comprising an alkyl chloride;
   transferring a portion of said composition to a second reactor; and
   adding concentrated hydrochloric acid to said second reactor, thereby forming a vapor comprising said alkyl chloride;
   wherein said alkyl chloride has 6–16 carbon atoms, and said reacting is carried out at a temperature below the normal boiling point of said alkyl chloride.

12. The process of claim 11, wherein said alkyl chloride has 6–10 carbon atoms.

13. The process of claim 11, wherein said reacting is carried out at 5°–100° C. below the normal boiling point of said alkyl chloride.

14. The process of claim 11, wherein said process is carried out continuously.

15. The process of claim 11, wherein said alkyl chloride is selected from the group consisting of n-hexyl chloride, n-octyl chloride, decyl chloride, dodecyl chloride and tetradecyl chloride.

16. The process of claim 11, wherein said alkyl chloride is a monochloride.

17. The process of claim 11, wherein said concentrated hydrochloric acid has a strength of 30–40%.

18. The process of claim 11, wherein said reacting takes place in the presence of a catalyst.

19. The process of claim 11, further comprising:
   condensing said vapor into a distillate comprising
      (i) a first phase comprising aqueous hydrochloric acid; and
      (ii) a second phase comprising said alkyl chloride; and
   adding said first phase to said composition.

20. The process of claim 11, wherein said process produces said alkyl halide in a yield of at least 95%, based on said alcohol.

* * * * *